(12) United States Patent
Biscotti

(10) Patent No.: US 7,223,226 B2
(45) Date of Patent: May 29, 2007

(54) BRACHYTHERAPY NEEDLE AND METHODS FOR ASSEMBLING SAME

(75) Inventor: Anthony Biscotti, Acton, MA (US)

(73) Assignee: Nuclear Consultants Group, Inc., Acton, MA (US)

( * ) Notice: Subject to any disclaimer, the term of this patent is extended or adjusted under 35 U.S.C. 154(b) by 0 days.

(21) Appl. No.: 11/267,753

(22) Filed: Nov. 4, 2005

(65) Prior Publication Data

US 2006/0100476 A1 May 11, 2006

Related U.S. Application Data

(60) Provisional application No. 60/625,227, filed on Nov. 5, 2004.

(51) Int. Cl.
*A61M 36/12* (2006.01)

(52) U.S. Cl. .......................... 600/7; 604/265; 604/266; 600/1; 600/3; 600/7

(58) Field of Classification Search ................ 600/1–8; 604/265–266
See application file for complete search history.

(56) References Cited

U.S. PATENT DOCUMENTS

| | | | |
|---|---|---|---|
| 4,697,575 A | 10/1987 | Horowitz | |
| 4,815,449 A | 3/1989 | Horowitz | |
| 6,450,937 B1 | 9/2002 | Mercereau et al. | |
| 6,450,938 B1 | 9/2002 | Miller | |
| 6,530,875 B1 | 3/2003 | Taylor et al. | |
| 6,554,760 B2 | 4/2003 | Lamoureux et al. | |
| 6,746,661 B2 | 6/2004 | Kaplan | |
| 6,997,862 B2 | 2/2006 | Terwilliger et al. | |
| 7,037,252 B2 | 5/2006 | Flanagan et al. | |
| 7,060,020 B2 | 6/2006 | Terwilliger et al. | |

FOREIGN PATENT DOCUMENTS

WO    2003028808 A2    4/2003

OTHER PUBLICATIONS

Nath R. et al., Code of practice for brachytherapy physics: Report of the AAPM Radiation Therapy Committee Task Force No. 56, Med. Phys. 24 (10):1557 -1598 (Oct. 1997).
Yu Y. et al., Permanent prostate seed implant brachytherapy: Report of the AAPM Radiation Therapy Committee Task Force No. 64, Med. Phys. 26 (10):2054 -2076 (Oct. 1999).
Butler W.M. et al., I-125 Rapid StrandTM loading technique, Radiation Oncology Investigations,4(1): 48-49, 1996.

*Primary Examiner*—Charles A. Marmor, II
*Assistant Examiner*—Christine D. Hopkins
(74) *Attorney, Agent, or Firm*—Brian M. Dingman, Esq.; Mirick, O'Connell, DeMallie & Lougee, LLP

(57) ABSTRACT

Needles and methods of plugging a needle having a tip opening with an inside diameter and a needle tip length, wherein the methods generally comprise the steps of, providing a plug material having a predetermined viscosity; providing a delivery device for introducing the plug material into the needle tip opening, wherein the delivery device comprises a delivery tube having a delivery diameter that is equal to or less than the inner diameter of the needle tip opening; introducing at least a portion of the heated plug material into the needle tip opening via the delivery tube.

18 Claims, 2 Drawing Sheets

BRACHYTHERAPY NEEDLE AND METHODS FOR ASSEMBLING SAME

CROSS-REFERENCE

This is a continuation-in-part of U.S. Provisional Patent Application Ser. No. 60/625,227 filed on Nov. 5, 2004.

FIELD OF THE INVENTION

This invention relates to brachytherapy needles and methods for assembling the needles.

BACKGROUND OF THE INVENTION

Brachytherapy needles, plugged with suppository material, bone wax or other bioabsorbable materials and then loaded with radioactive seeds, are known in the art. However there are numerous problems associated with loading and plugging the needles. Problems with the current art of plugging the distal end of a needle with a pre-shaped cylindrical plug stem from the fact that the plug does not exactly take on the inner shape of the needle as a liquid would. As needles are manufactured, the inside diameter (ID) has a plus/minus tolerance. In addition, pre-formed cylindrical plugs may also vary in size. As a result of these to variables in the needles and plugs, the fit between the needles and the plugs may be compromised which often causes a variable and therefore uncontrolled push out pressure or plug failure when the plug is ejected from the needle via a stylet. To overcome this issue, manufacturers have added mechanical "crutches" to aid in the retention of the plug such as indentations or "U" shaped tabs cut into the needle wall and protruding into the ID of the needle in the area the plug will be placed to compensate for this problem. The additional manufacturing complexities drive the production cost of the needle higher. Additionally, "U" shaped tabs do not prevent bodily fluids from traveling up the needle.

There are additional problems with the "one size fits all plug." These plugs result in push out pressures that are not easily adjustable to the different needs in the market. The radioactive seeds, known as brachytherapy seeds, are often times prepared in a "strand", inserted into a pre-plugged needle for implantation and expelled into the appropriate organ to be treated. The various stranding materials in the market are constructed differently and may jam in the needle if the operator of the needle has to apply too much pressure to release the plug.

Alternatives to preformed plugs are pliable bone wax plugs and molten liquids. However there are also several problems associated with the use of pliable bone wax and molten liquids. The plugging material not only sticks to the inside of the needle, but the outside as well, as the needle is "dipped" or pushed into a container of molten liquid or block of bone wax. This requires the assembler of the needle to "wipe" the exterior "clean" of the residual material. The length of bone wax plugs may also unpredictably vary. Additionally, oftentimes the configuration of seeds and spacers needs to be removed and repositioned. However, as the once loaded seeds are expelled from the needle, the seeds now have bone wax on them that has to be removed from the seeds prior to re-inserting them into a new needle for implantation. If the bone wax is not removed the seed will be very difficult to handle, sticking to the loading tool and the needle into which they are to be re-loaded. Seeds loaded into needles that are plugged, using the dipping method and molten suppository material having lower molecular weight PEG, will have the same issue due to the naturally sticky state of this material at room temperature. Lower molecular weight PEG formulations also will not retain their shape under the temperatures some times seen with sterilization (about 50° C.) as would PEG of higher molecular weights such as PEG 8000 for example. If the plug melts during the sterilization of the pre-loaded needle the seeds will fall out.

SUMMARY OF THE INVENTION

It is therefore a primary object of this invention to provide a brachytherapy needle with a plug that is seated firmly within the needle yet can be readily pushed out to release the seeds during implantation.

It is a further object of the invention to provide a method for plugging the needle that is efficient and facilitates repeatable quality control.

It is a further object of the invention to provide a plug that will not stick to the seeds at room temperatures and will withstand the heats seen during sterilization.

The invention features a unique method for plugging brachytherapy needles. The resulting loaded and plugged needle and the preferred method of loading and assembling of the invention were developed to provide, not only an improved method for plugging needles, but also an improved brachytherapy needle. The plugged needle of the invention enables a doctor to more readily predict the amount of pressure needed to release the seeds from the needle and the peace of mind that all of the seeds remain after implantation at their preplanned positions.

One preferred method of the invention features a heating gun that is used to melt carefully selected amounts and formulations of polyethylene glycol (PEG) and then to release the molten PEG directly into the inside of the needle tip. The molten PEG then solidifies within the needle tip and adheres to the inside surface of the needle. As such, the mechanical means of retaining the preformed plugs of the prior art in the needle, such as frustoconical tongues that protrude inward within the cannula body, are not necessary with the PEG plugs of the invention. The amount of PEG inserted into the needle can be preselected to provide a shorter or longer plug as needed. Moreover, the formulation of the PEG can be selected, modified, and adapted as needed to provide predictable push out pressures by varying the viscosity and adhesiveness of the PEG as needed.

Polyethylene Glycol (PEG) has long been used in the pharmaceutical industry as the base material for delivering medications rectally in suppositories. PEG is available in different molecular weights. Different molecular weights result in the PEG having a different state of hardness varying from a slightly viscous solution at lower molecular weights, to very hard.

A preferred embodiment of the method of the invention for plugging a needle having a tip opening with an inside diameter and a needle tip length, generally comprises the steps of, providing a plug material having a predetermined viscosity; providing a means for introducing the plug material into the needle tip opening wherein the means comprises a delivery tube having a delivery diameter that is equal to or less than the inner diameter of the needle tip opening; introducing at least a portion of the heated plug material into the needle tip opening via the delivery tube. The means for introducing preferably further comprises a means for delivering a predetermined volume amount of the plug material into the needle tip corresponding to the needle tip length.

The method may further comprises the step of calibrating the means for introducing to introduce reproducible predetermined amounts of the plug material into a plurality of needles, wherein the means for introducing the predetermined amount preferably comprises a trigger.

The means for introducing may still further comprise a means for heating the plug material, and further comprising the step of heating the plug material with the means for heating. This latter means is particularly suited for methods in which the plug material comprises polyethylene glycol (PEG). As noted, a variety of PEG compositions may be used however one preferred PEG formulation comprises PEG 8000. The plug material may also comprise additional materials to increase the melting temperature of the PEG selected and/or an antibacterial agent.

The step of providing the plug material may comprise the steps of, heating a crystalline PEG material to a temperature sufficient to melt the PEG and to kill any bacteria present; introducing the molten PEG into one or more molds; solidifying the PEG in the molds; removing the molded PEG from the molds, wherein the molded PEG preferably has a predetermined length and diameter.

The means for introducing preferably comprises a gun, in which instance the method may further comprise the step of loading the provided plug material into the gun, and wherein the step of introducing is carried out under sterile conditions.

The preferred plugged needle of the invention is made using the methods of the invention and generally comprises a plurality of brachytherapy seeds and plug material, wherein the plug material preferably provides a predetermined push out pressure.

Another preferred method of the invention for plugging a needle having a tip opening with an inside diameter and a needle tip length, generally comprises the steps of, providing a bio-compatible plug material having a predetermined molecular weight; providing a means for. introducing the plug material into the needle tip opening wherein the means comprises a delivery tube having a delivery diameter that is equal to or less than the inner diameter of the needle tip opening; introducing at least a portion of the heated plug material into the needle tip opening via the delivery tube. This method may also further comprise the step of calibrating the means for introducing to introduce reproducible predetermined volume amounts of the plug material into a plurality of the needles. Another preferred embodiment of the needle of the invention is made using this method and generally comprises a plurality of brachytherapy seeds and the plug material.

The plug material used in the methods and needles of the invention may comprise a variety of bio-absorbable materials such as those selected from a group consisting of PEG, Floseal® (bio-absorbable sealant comprising thrombin and gelatin), and silicone.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS AND METHODS

The methods of the invention provide novel ways in which to plug needles. One preferred method utilizes a heating gun for, not only heating the plug material, but also to deliver or otherwise introduce the plug material into the tip of the needle. Another preferred method utilizes a gun to meter out the amount of plug material introduced into the needle tip without the need to heat the plug material.

As noted, polyethylene glycol (PEG) has long been used in the pharmaceutical industry as the base material for delivering medications rectally in suppositories. Although PEG has been used in the past to seal, or otherwise create a skin at, the ends of the needles by dipping the needle tips into molten PEG, such methods require the assembler of the needle to "wipe" the exterior "clean" of the residual material.

However, there are at least two characteristics of PEG that make it an attractive potential tool for sealing the ends of needles while resolving all the previous problems associated with PEG seals. PEG is available in different molecular weights. Different molecular weights enables a user to pre-select the PEG material to form different states of hardness varying from a slightly viscous solution having a lower molecular weight to a very hard material having a higher molecular weight. PEG is also well suited for plugging brachytherapy needles because of the range of PEG melting points. As the molecular weight of PEG increases, the melting point also increases. As such, combinations of PEG compositions, having different molecular weights, may be combined to produce a resulting mixture with characteristics hardness and melting points tailored to the requirements of the application.

Figure 1:
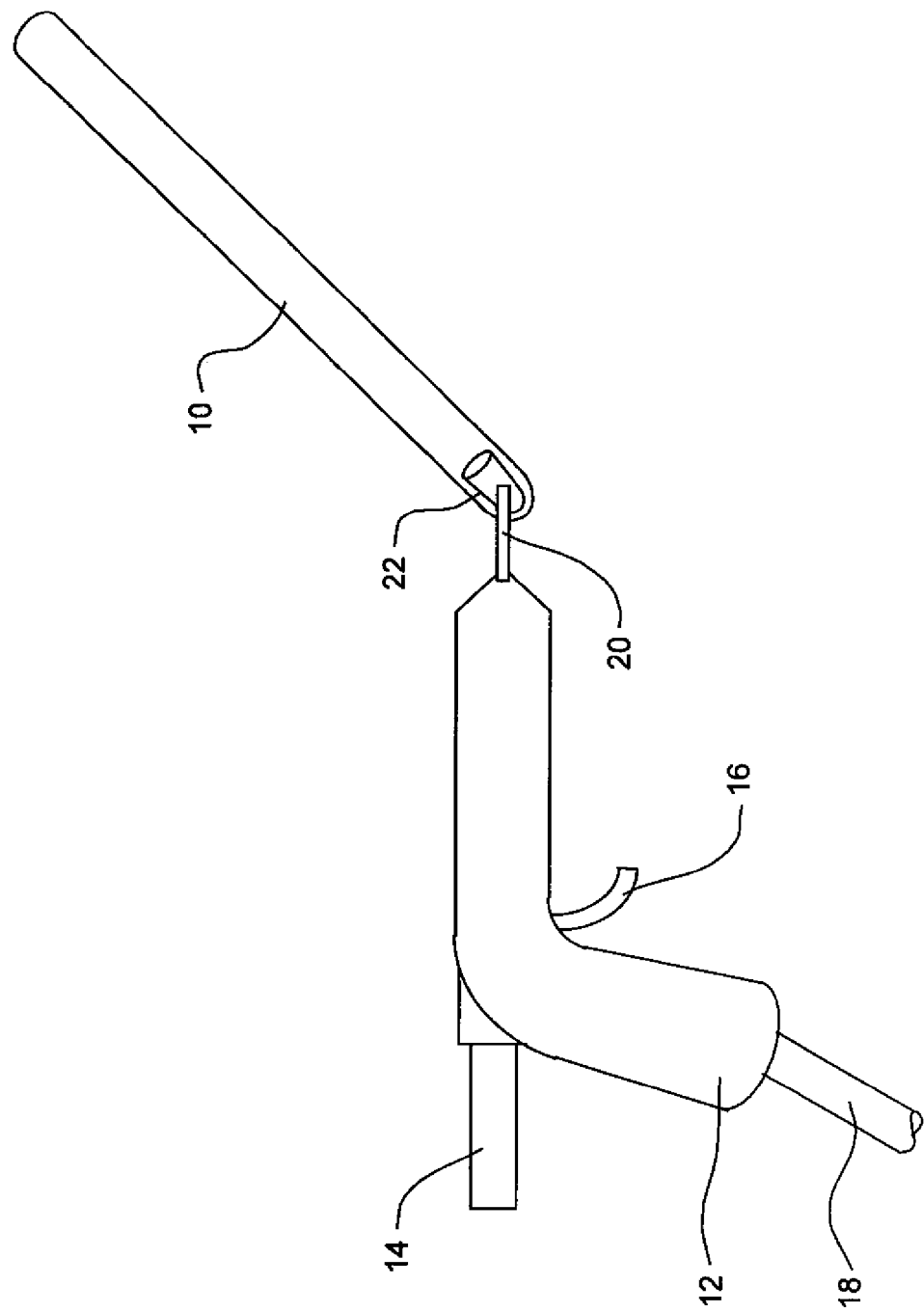
FIG. 1 is a schematic view of the gun and needle as the gun is employed to plug the needle of the invention using the method of the invention.
Figure 2:
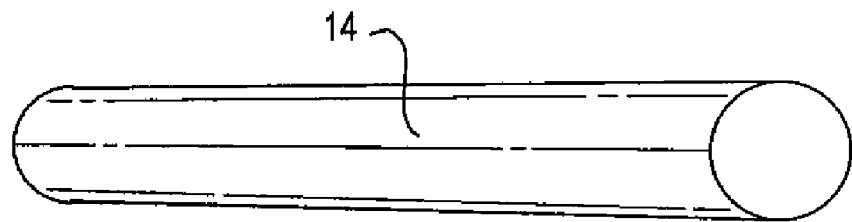
FIG. 2 is a perspective view of a pre-form PEG cylinder used to load the heat gun employed in the method of the invention.

The tools utilized in the method of the invention are schematically shown in FIG. 1. The needle and methods of the invention employ a novel gun with a heated barrel. As shown in FIG. 1, heating gun 12 is used to melt and release the molten PEG into needle 10. A pre-formed PEG cylinder 14, molded from a predetermined formulation based on the requirements of the application, is loaded into the barrel of heating gun 12. Gun 12 is adapted to accept a specifically sized PEG rod loaded into the rear barrel of the gun. The gun then feeds a specific length of the preformed PEG rod into a heating element as trigger 16 is pulled. Thus, only a small predetermined section length of the solid PEG rod is melted and then immediately expelled out through the front barrel of the gun through tube 20. Tube 20 has an outer diameter that is smaller than the inner diameter of needle 10. This method allows the molten material to be delivered to the inside of the needle while the outside of the needle tip 28 is free from unwanted residual material. The trigger or feeder on the heat gun is calibrated to yield reproducible volumes of molten PEG upon activation of the trigger feeder.

Figure 3:
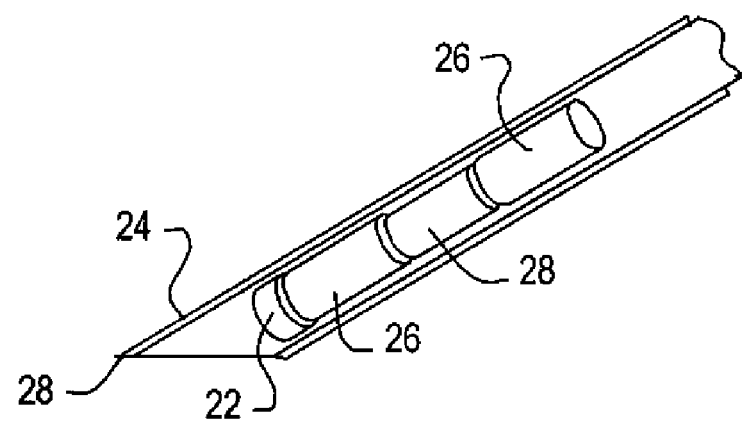
FIG. 3 is a partial perspective view of the tip of the needle after it has been plugged using the method of the invention.

The solidified PEG plug 22 is shown in FIG. 3, seated within, and fixed in place by adhesion to the inside wall of, cannula 24. Seeds 26, separated by spacer 28, are retained inside the cannula until pushed out during implantation.

EXAMPLE

In a glass beaker add 50 grams of PEG 8000 and an antibacterial agent if desired. Heat the PEG formulation to a predetermined temperature for the required time, based on the formulation, to melt the crystalline PEG into a molten liquid. The mixture should be brought to a specific temperature for a specific time to kill all bacteria present, if desired. Pour the molten PEG into sterilized cylindrical shaped molds in a class 100 laminar flow hood. Let the filled mold cool to room temperature. Wearing sterile rubber gloves, remove the PEG cylinders (about 2.5 inches long and having a diameter of about ¼ inch) from the mold.

Once the cylinder is solidified, load the cylindrical rod of PEG into the calibrated PEG heat gun. Activate the trigger until molten PEG appears at the tip of the gun barrel to ensure the gun is at the proper temperature to melt the PEG. Clean the barrel of any excess PEG and insert the barrel tube into the sharpened end of the needle to be plugged. Activate trigger to deposit a droplet of PEG. Remove barrel from needle tip and repeat on the next needle.

Another preferred method of the invention utilizes other FDA approved bio-absorbable implantable materials as plug materials that do not need to be heated before introducing the plug material into the needle tip. Such bio-absorbable material includes, but is not limited to, Floseal® (bio-absorbable sealant comprising thrombin and gelatin) which is normally used to close wounds, and liquid silicone that is cured, or otherwise hardened, upon exposure to air, heat, and/or various light sources. Such other bio-absorbable materials are preferably introduced using a gun, similar to gun 12, but without the need for a heating element in the gun. The gun still preferably is fitted to deliver a predetermined amount of plug material into the needle tip and may similarly be calibrated to deliver reproducible amounts of material into successive needle tips.

Virtually all, if not all, of the steps of the methods of the invention are preferably performed under sterile conditions. Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A method of plugging a needle having a tip opening with an inside diameter and a needle tip length, comprising the steps of,
   providing a plug material having a predetermined viscosity;
   providing a means for introducing said plug material into said needle tip opening wherein said means comprises a delivery tube having a delivery diameter that is equal to or less than said inner diameter of said needle tip opening;
   introducing at least a portion of said plug material into said needle tip opening via said delivery tube.

2. The method of claim 1, wherein said means for introducing further comprises a means for delivering a predetermined amount of said plug material into said needle tip corresponding to said needle tip length.

3. The method of claim 2, further comprising the step of calibrating said means for introducing to introduce reproducible predetermined amounts of said plug material into a plurality of needles.

4. The method of claim 2, wherein said means for introducing said predetermined amount comprises a trigger.

5. The method of claim 1, wherein said means for introducing further comprises a means for heating said plug material, and further comprising the step of heating said plug material with said means for heating.

6. The method of claim 5, wherein said plug material comprises polyethylene glycol (PEG).

7. The method of claim 6, wherein said PEG comprises PEG 8000.

8. The method of claim 1, further comprising the step of solidifying said plug material after it is introduced into said needle tip.

9. The method of claim 1, wherein said plug material comprises an antibacterial agent.

10. The method of claim 1, wherein said step of providing further comprises the steps of,
    heating a crystalline PEG material to a temperature sufficient to melt said PEG and to kill any bacteria present;
    introducing said molten PEG into one or more molds;
    solidifying said PEG in said molds;
    removing said molded PEG from said molds.

11. The method of claim 10, wherein said molded PEG has a predetermined length and diameter.

12. The method of claim 1, wherein said means for introducing comprises a gun, and further comprises the step of loading said provided plug material into said gun, and wherein said step of introducing is carried out under sterile conditions.

13. A needle plugged using the method of claim 1 comprising a plurality of brachytherapy seeds and said plug material.

14. The needle of claim 13, wherein said plug material provides a predetermined push out pressure.

15. A method of plugging a needle having a tip opening with an inside diameter and a needle tip length, comprising the steps of,
    providing a bio-compatible plug material having a predetermined molecular weight;
    providing a means for introducing said plug material into said needle tip opening wherein said means comprises a delivery tube having a delivery diameter that is equal to or less than said inner diameter of said needle tip opening;
    introducing at least a portion of said plug material into said needle tip opening via said delivery tube.

16. The method of claim 15, wherein said plug material comprises bio-absorbable material selected from a group consisting of PEG, bio-absorbable sealant comprising thrombin and gelatin, and silicone.

17. The method of claim 16, further comprising the step of calibrating said means for introducing to introduce reproducible predetermined amounts of said plug material into a plurality of said needles.

18. A needle plugged using the method of claim 15 comprising a plurality of brachytherapy seeds and said plug material.

* * * * *